United States Patent

Bonicel

[11] Patent Number: 5,243,670
[45] Date of Patent: Sep. 7, 1993

[54] OPTICAL FIBER MOISTURE SENSOR
[75] Inventor: Jean-Pierre Bonicel, Lyons, France
[73] Assignee: Alcatel Cable, Clichy Cedex, France
[21] Appl. No.: 922,476
[22] Filed: Jul. 31, 1992
[30] Foreign Application Priority Data Aug. 2, 1991 [FR] France ................... 91 09890

[51] Int. Cl.⁵ .................................................. G02B 6/00
[52] U.S. Cl. ..................... 385/13; 250/227.14
[58] Field of Search ............... 385/12, 13; 250/227.14, 250/227.15

[56] References Cited

U.S. PATENT DOCUMENTS

| 4,221,962 | 9/1980 | Black et al. | 250/227.25 |
| 4,530,078 | 7/1985 | Lagakos et al. | 385/13 |
| 4,637,729 | 1/1987 | Schoch | 250/227.25 |
| 4,652,745 | 3/1987 | Zanardelli | 250/227.25 |
| 4,729,630 | 3/1988 | Martinez | 385/13 |
| 4,866,265 | 9/1989 | Hohne | 250/227 |
| 4,918,305 | 4/1990 | Wlodarczyk et al. | 250/227.14 |

FOREIGN PATENT DOCUMENTS

| 86024 | 8/1983 | . | |
| 240100 | 10/1987 | . | |
| 357253 | 3/1990 | European Pat. Off. . | |
| 3327158 | 2/1985 | Fed. Rep. of Germany . | |
| 2-28611 | 9/1990 | Japan | 385/13 |

OTHER PUBLICATIONS

Izutsu et al., *Journal of Lightwave Technology*, vol. LT-4, No. 7, Jul. 1986, "Integrated Optic Temperature and Humidity Sensors", pp. 833-836.

*Primary Examiner*—Frank Gonzalez
*Attorney, Agent, or Firm*—Sughrue, Mion, Zinn, Macpeak & Seas

[57] ABSTRACT

An optical fiber moisture sensor comprising a mechanical system having a stationary jaw and a moving jaw between which said fiber is mounted, the sensor also including an element made of moisture-sensitive material coupled to said moving jaw to allow it to be urged towards said stationary jaw in the presence of moisture, thereby applying compression to said optical fiber, wherein said element is made of a material that looses mechanical strength with increasing moisture and that is mounted to oppose the action of resilient means urging said moving jaw towards said stationary jaw.

11 Claims, 1 Drawing Sheet

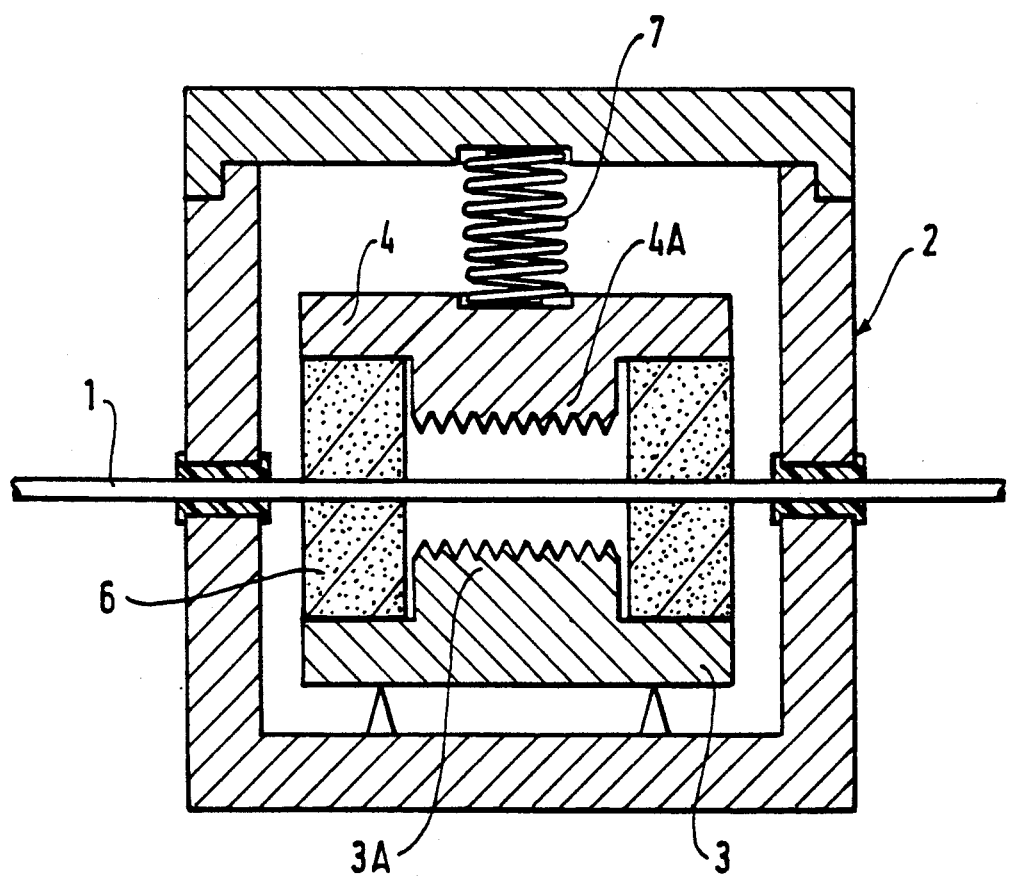

OPTICAL FIBER MOISTURE SENSOR

The present invention relates to moisture sensors using an optical fiber and designed to enable the state of optical links to be monitored. Such sensors are used in particular at special points on an optical connection, such as splice boxes, where possible ingress of water or moisture is prejudicial to the quality of transmission. Such sensors may also be used in any kind of industrial system that requires monitoring for moisture or water.

BACKGROUND OF THE INVENTION

Optical fiber sensors, per se, are already known. They use a material which, in the presence of moisture, absorbs the moisture and swells, thereby compressing an optical fiber to a greater or lesser extent as a function of the amount of moisture absorbed, which fiber is used for monitoring the connection. The stress applied to the optical fiber gives rise to a local attenuation in transmission and this is detected.

The article entitled "Optical fiber line support system" published in NTT Review, Vol. 3, No. 1, January 1991 describes such a sensor. The optical fiber passes through a mechanical system having a stationary jaw and a moving jaw between which the fiber passes, and having absorbent material that swells in the presence of moisture, thereby optionally actuating the moving jaw. The system applies no stress on the fiber in the absence of any absorbed moisture, and it compresses it with increasing moisture absorption by the material.

That system has the advantage of being particularly simple. However, its reaction time is relatively long and it is not very accurate when it comes to monitoring quickly-varying stresses due to variations in ambient humidity which may be prejudicial to the quality of transmission on the optical line monitored by means of the sensor.

An object of the present invention is to remedy these drawbacks.

SUMMARY OF THE INVENTION

The present invention provides an optical fiber moisture sensor comprising a mechanical system having a stationary jaw and a moving jaw between which said fiber is mounted, the sensor also including an element made of moisture-sensitive material coupled to said moving jaw to allow it to be urged towards said stationary jaw in the presence of moisture, thereby applying compression to said optical fiber, wherein said element is made of a material that losses mechanical strength with increasing moisture and that is mounted to oppose the action of resilient means urging said moving jaw towards said stationary jaw.

The sensor of the present invention preferably also includes at least one of the following features:

said element made of moisture-sensitive material is mounted as a spacer between said jaws, thereby moving them apart against the action of said resilient element without compressing said fiber in the absence of moisture, but at least partially releasing the action of said resilient element in the presence of moisture;

the said material is selected from materials based on cellulose, polyacrylamide, saccharose, and carbon hydrate, in particular; and the said optical fiber is an optical fiber independent from an optical link being monitored or it is one of the optical fibers of said optical link being monitored.

BRIEF DESCRIPTION OF THE DRAWING

An embodiment of the invention is described by way of example with reference to the sole FIGURE of the accompanying drawing.

DETAILED DESCRIPTION

In the sole FIGURE, the moisture sensor has an optical fiber 1. It is mounted in a box 2. The box is not watertight. In particular, the box 2 also contains splices between two lengths in a multifiber optical connection to be monitored, with the sensor being associated therewith in use. The optical fiber 1 may be a fiber independent from the connection being monitored and it may be a monomode or a multimode monitoring fiber. Alternatively, it may be a fiber belonging to the connection being monitored, being a monomode fiber or a multimode fiber, that is used at a first wavelength for transmission purposes, and at a second wavelength for monitoring purposes.

The sensor is constituted by a mechanical system for compressing the optical fiber 1 as a function of the moisture in the box 2. It comprises a stationary jaw 3 and a moving jaw 4 on opposite sides of the optical fiber 1 which passes between them. Each of these two jaws has a middle side shoulder 3A or 4A on its side facing the other jaw, which shoulder is itself serrated as shown, or corrugated, or merely convex, being smooth or otherwise.

The stationary jaw is carried by one of the walls of the box and it is held stationary relative to said wall. The moving jaw is urged by resilient means towards the stationary jaw. It is held relative to said stationary jaw against said resilient means by a counteracting element whose counteraction varies with moisture conditions, having high mechanical strength in the absence of moisture in the box but loosing said mechanical characteristic with increasing moisture.

In the embodiment shown, this counteracting element is mounted to hold the jaws apart and is constituted by two pairs of spacers or abutments 6 or by two spacing rings between the jaws 3 and 4 that act against a compression spring 7. The spring 7 is mounted between the moving jaw and the facing wall of the box.

This counteracting element is made of a material based on cellulose, polyacrylamide, saccharose, or a carbon hydrate, in particular, having high mechanical strength when dry but loosing strength in the presence of and as a function of ambient moisture, such that its strength may become substantially zero, thereby releasing the resilient element to act correspondingly on the moving jaw.

Any such mechanical stress exerted on the optical fiber 1 is detected and located by backscattering, in particular.

Naturally, any other equivalent disposition of the resilient element and of the counteracting element could be adopted without going beyond the ambit of the present invention, providing said counteracting element opposes the action of the resilient element when dry and offers reduced mechanical opposition thereto in the presence of moisture.

I claim:

1. An optical fiber moisture sensor comprising a mechanical system having a stationary jaw and a moving jaw between which an optical fiber is mounted, the sensor also including an element made of moisture-sensitive material coupled to said moving jaw to allow said moving jaw to be urged towards said stationary jaw in the presence of moisture, thereby applying compression to said optical fiber, wherein said element is made of a material that looses mechanical strength with increasing moisture and that is mounted to oppose the action of resilient means urging said moving jaw towards said stationary jaw.

2. A sensor according to claim 1, wherein said element made of moisture-sensitive material is mounted as a spacer between said jaws.

3. A sensor according to claim 1, wherein at least one of said jaws has a shoulder facing the other jaw.

4. A sensor according to claim 3, wherein the edge of said shoulder is serrated, or corrugated, and/or convex.

5. A sensor according to claim 1, wherein said element of moisture-sensitive material is made of a material defined by materials based on cellulose, polyacrylamide, saccharose, and carbon hydrate.

6. A sensor according to claim 1, wherein said optical fiber is independent of an optical link monitored by means of said sensor.

7. A sensor according to claim 1, wherein said optical fiber belongs an optical link monitored by means of said sensor.

8. A sensor according to claim 6, wherein said optical fiber is monomode.

9. A sensor according to claim 6, wherein said optical fiber is multimode.

10. A sensor according to claim 7, wherein said optical fiber is monomode.

11. A sensor according to claim 7, wherein said optical fiber is multimode.

* * * * *